(12) United States Patent
Heitsman et al.

(10) Patent No.: US 11,161,410 B2
(45) Date of Patent: Nov. 2, 2021

(54) MACHINE CONTROL USING BIOMETRIC RECOGNITION

(71) Applicant: Deere & Company, Moline, IL (US)

(72) Inventors: Joshua C. Heitsman, Princeton, IA (US); Reginald M. Bindl, Bettendorf, IA (US); Keith N. Chaston, Dubuque, IA (US); Michael G. Kean, Maquoketa, IA (US); John M. Hageman, Dubuque, IA (US); Mark J. Cherney, Potosi, WI (US); Sean P. West, Dubuque, IA (US)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 16/825,656

(22) Filed: Mar. 20, 2020

(65) Prior Publication Data

US 2020/0223312 A1    Jul. 16, 2020

Related U.S. Application Data

(63) Continuation of application No. 16/248,011, filed on Jan. 5, 2019, now Pat. No. 10,723,226.

(51) Int. Cl.
| | |
|---|---|
| *B60K 28/06* | (2006.01) |
| *G06K 9/46* | (2006.01) |
| *G06F 21/32* | (2013.01) |
| *G08B 21/06* | (2006.01) |
| *B60W 40/08* | (2012.01) |
| *A61B 3/113* | (2006.01) |

(52) U.S. Cl.
CPC ............ *B60K 28/066* (2013.01); *G06F 21/32* (2013.01); *G06K 9/4609* (2013.01); *G08B 21/06* (2013.01); *A61B 3/113* (2013.01); *B60W 2040/0809* (2013.01); *B60W 2040/0827* (2013.01)

(58) Field of Classification Search
CPC .. A01B 69/00; B60K 2370/146; B60K 28/06; B60K 28/066; B60K 35/00
See application file for complete search history.

(56) References Cited

U.S. PATENT DOCUMENTS

| | | | |
|---|---|---|---|
| 9,809,115 B2 | 11/2017 | Mader et al. | |
| 10,723,226 B1 | 7/2020 | Heitsmnan et al. | |
| 2008/0297330 A1* | 12/2008 | Jeon | B60R 25/25 340/426.11 |
| 2009/0248285 A1* | 10/2009 | Bauer | G08G 1/096838 701/117 |
| 2014/0276090 A1* | 9/2014 | Breed | A61B 5/14546 600/473 |
| 2017/0008490 A1* | 1/2017 | Sako | B60R 25/25 |
| 2017/0088147 A1 | 3/2017 | Tentinger et al. | |
| 2019/0056732 A1* | 2/2019 | Aoi | B60W 50/14 |
| 2019/0080069 A1* | 3/2019 | Sato | G09B 19/14 |
| 2019/0196462 A1* | 6/2019 | Bolz | G06F 1/163 |

FOREIGN PATENT DOCUMENTS

| | | |
|---|---|---|
| CM | 107554483 A | 1/2018 |
| WO | 17058553 A1 | 4/2017 |

* cited by examiner

*Primary Examiner* — Omeed Alizada
(74) *Attorney, Agent, or Firm* — Joseph R. Kelly; Kelly, Holt & Christenson PLLC

(57) ABSTRACT

A pattern recognition system receives an image captured by an image capture device, of an operator and the operator is identified. Operator information is accessed, based upon the identified operator, and a control signal is generated to control a mobile machine, based upon the operator information.

19 Claims, 11 Drawing Sheets

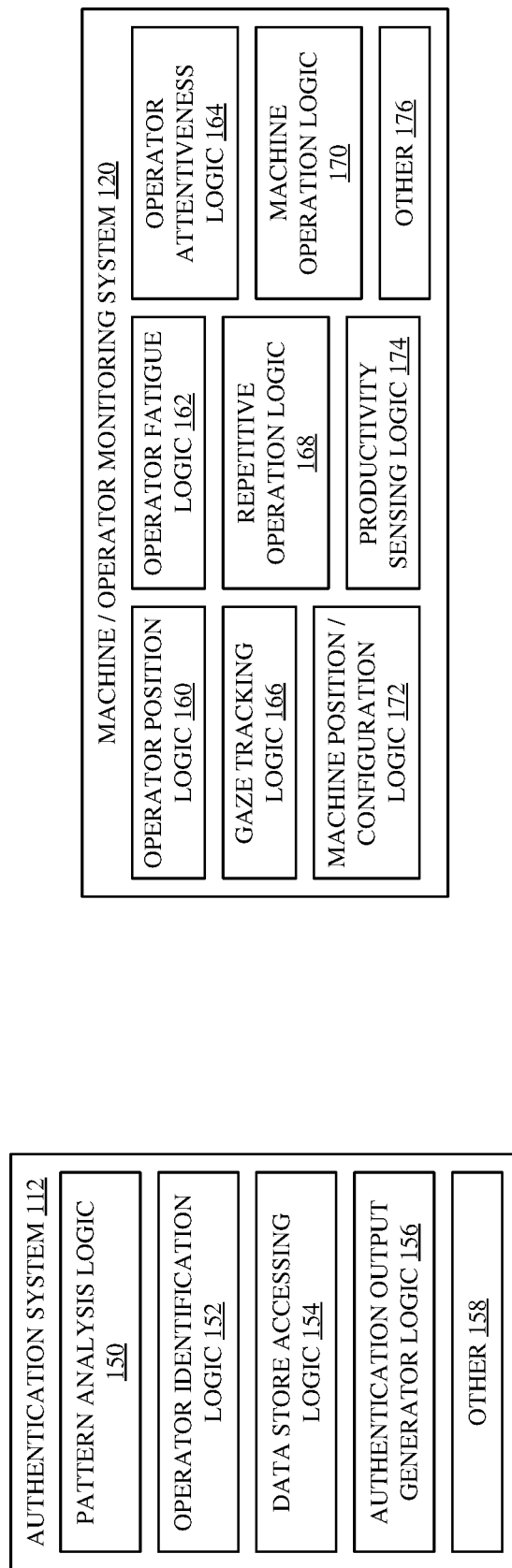

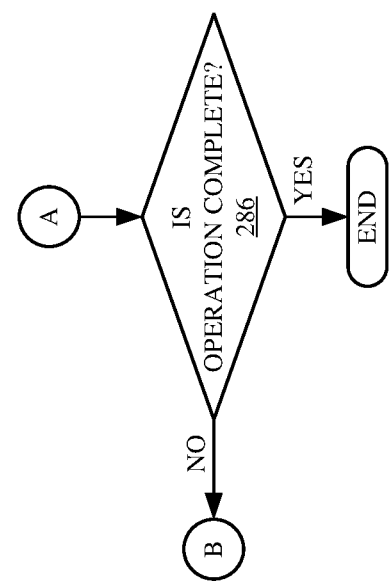

MACHINE CONTROL USING BIOMETRIC RECOGNITION

CROSS-REFERENCE TO RELATED APPLICATION

The present application is a continuation of and claims priority of U.S. patent application Ser. No. 16/248,011, filed Jan. 15, 2019, the content of which is hereby incorporated by reference in its entirety.

FIELD OF THE DESCRIPTION

The present description relates to mobile construction machines and other mobile work machines. More specifically, the present description relates to capturing an image of, or sensing another biometric characteristic of, an operator and controlling the mobile work machine based upon the captured image or other sensed biometric characteristic.

BACKGROUND

There are a wide variety of different types of mobile work machines (or mobile machines). Some such machines include construction machines, agricultural machines, forestry machines, turf management machines, among others.

It is not uncommon for such machines to be deployed at a worksite (such as a construction site, a forestry site, etc.) and to be operated by a number of different operators at that same site. Similarly, it is not uncommon for the different operators to have different skill levels in operating the machines.

The discussion above is merely provided for general background information and is not intended to be used as an aid in determining the scope of the claimed subject matter.

SUMMARY

A pattern recognition system receives an image, captured by an image capture device, of an operator, and the operator is identified. Operator information is accessed, based upon the identified operator, and a control signal is generated to control a mobile machine, based upon the operator information.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 2A is a block diagram showing one example of an authentication system, in more detail.

FIG. 2B is a block diagram showing one example of a machine/operator monitoring system, in more detail.

FIGS. 3A and 3B (collectively referred to herein as FIG. 3) show one example of the operation of a mobile machine, based upon a captured image.

DETAILED DESCRIPTION

Figure 1:
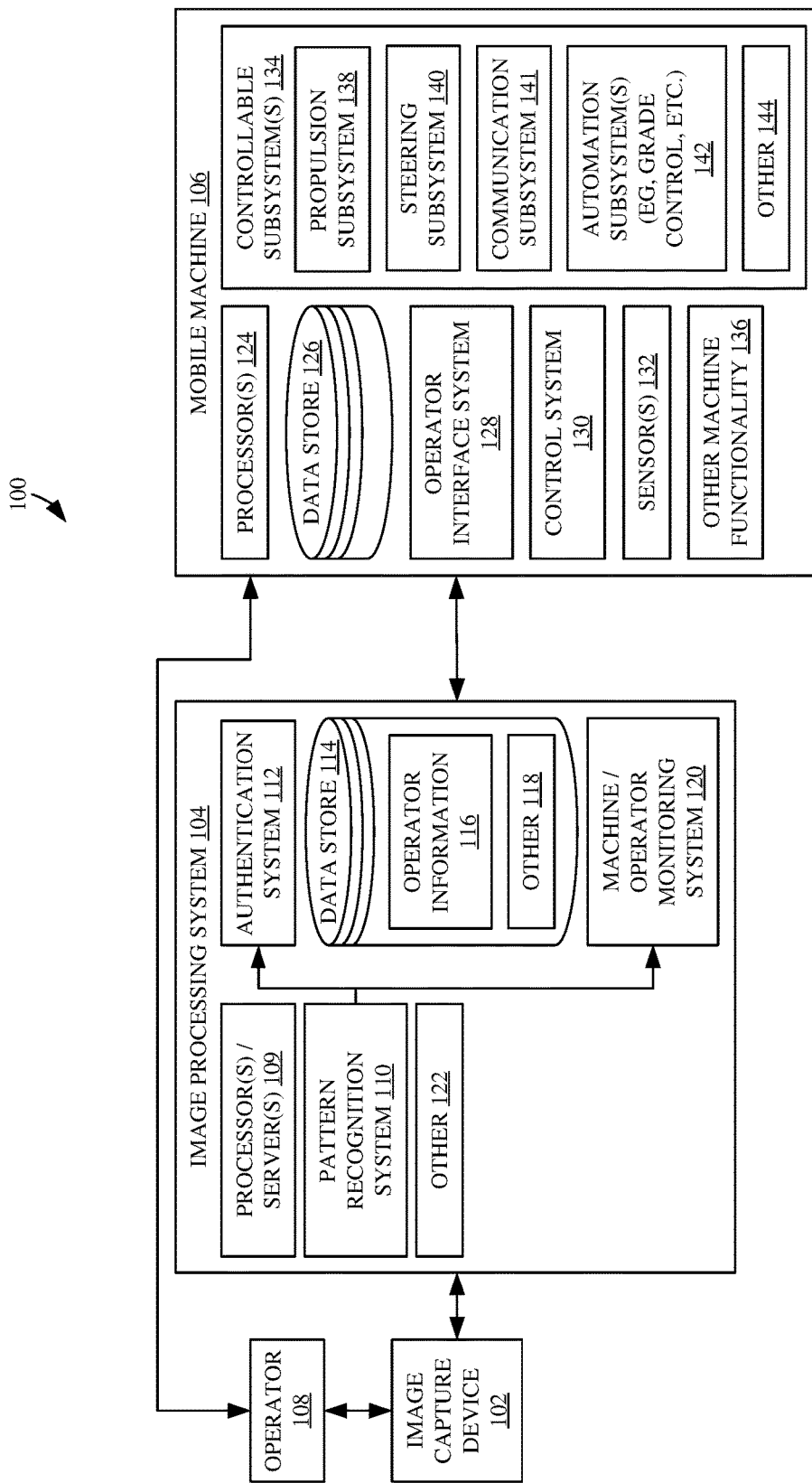
FIG. 1 is a block diagram of one example of a mobile machine architecture.

FIG. 1 is a block diagram showing one example of a mobile machine architecture 100. Architecture 100 illustratively includes image capture device 102, image processing system 104, and mobile machine 106. FIG. 1 also shows that an operator 108 can provide operator inputs to operate mobile machine 106. This can be done directly, over a network, or in other ways. Mobile machine 106 may be, for instance, a construction machine, such as a grader, an articulated loader, any of a variety of different types of dump trucks or other loaders, an excavator, etc. Where it is an agricultural machine, it can include a combine harvester, a tractor, or any of a wide variety of other planting, tillage, application, or other machines. Where it is a forestry machine, it may include such things as a skidder, a knuckle boom loader, a feller buncher, or other machines. These are examples only.

Briefly, by way of overview, image capture device 102 illustratively captures an image of operator 108 (such as a facial image, a retinal scan, or other biometric or image information). Image processing system 104 processes the image and can perform a number of operations. It can identify authenticating information corresponding to operator 108 and use that information to unlock various different types of functionality on mobile machine 106. It can also use that information to set settings on mobile machine 106 and to otherwise control mobile machine 106.

Similarly, image processing system 104 can continue to receive images of operator 108 and perform monitoring of either or both machine 106 and the operator 108. By way of example, it may identify, in the image, that operator 108 is inattentive (such as by being distracted with the operator's mobile device, by being fatigued, etc.). Based upon this continued monitoring, image processing system 104 can provide an input to mobile machine 106 to control mobile machine 106 based upon that information.

Figure 5:
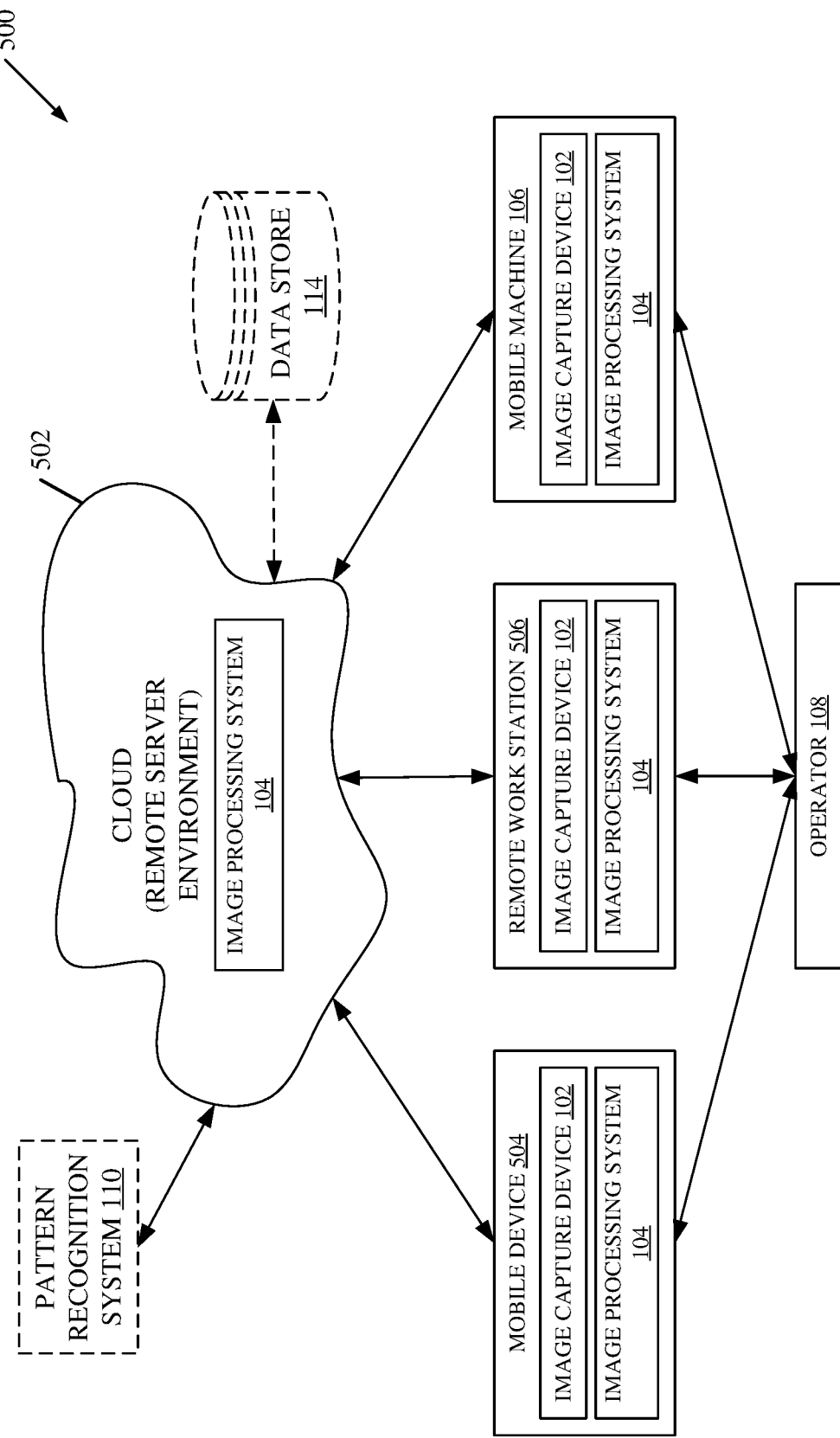
FIG. 5 is a block diagram showing different examples of the architecture illustrated in FIG. 1, deployed in a remote server architecture.

It will also be noted that the various items in FIG. 1 can be located in a variety of different places. For instance, it may be that operator 108 will reside in the operator compartment of mobile machine 106, and operate mobile machine 106 from there. In another example, it may be that operator 108 resides at a remote control station (one of which is shown in FIG. 5 below) where operator 108 provides inputs to the remote control station. The remote control station may then communicate those control inputs to mobile machine 106 over a network (such as a wide area network) or otherwise. Similarly, image capture device 102 may be on a mobile device, or other device, carried by operator 108. In another example, image capture device 102 may be on mobile machine 106 or at a remote control station that is used by operator 108 to control mobile machine 106. Where image capture device 102 is on mobile machine 106, it may be a camera that is arranged to capture an image of operator 108 as operator 108 approaches the operator compartment. It may be another pre-existing camera (such as a backup camera, a side view camera, etc.). In that case, it may be that operator 108 is instructed to stand at a certain location relative to machine 106 so that the image can be captured.

Image processing system 104 can reside in a variety of different locations as well. For instance, it can be on a mobile device carried by operator 108. It can be at a remote control station that operator 108 uses to remotely control machine 106. Image processing system 104 can also reside on mobile machine 106, itself, or it can reside on a remote system (such as a system located in a cloud architecture, or other remote server architecture, or elsewhere).

Before describing the operation of architecture 100 in more detail, a brief description of some of the items in architecture 100, and their operation, will first be provided. In the example shown in FIG. 1, image capture device 102 can be any of a wide variety of different devices that can be used to capture an image for processing. For instance, it can be a camera, a retinal scanner, or any other image capture device that can capture information used for processing as described herein. Image processing system 104, in the example shown in FIG. 1, includes processors or servers 109, pattern recognition system 110, authentication system 112, data store 114 (which, itself, includes operator information 116 and can include other items 118), machine/operator monitoring system 120, and it can include a wide variety of other items 122. Mobile machine 106 can include one or more processors 124, data store 126, operator interface system 128, control system 130, one or more sensors 132, controllable subsystems 134, and it can include a wide variety of other machine functionality 136. Controllable subsystems 134 can includes such things as a propulsion subsystem 138, steering subsystem 140, communication subsystem 141, automation subsystems (e.g., grade control, etc.) 142, and it can include a wide variety of other controllable subsystems 144.

Operator interface system 128 illustratively generates operator interfaces and includes operator interface mechanisms, for interaction by operator 108. Where operator 108 is in the operator compartment of mobile machine 106, the operator interface system can generate operator interfaces that are visual, audio, haptic, etc. The operator input mechanisms can include such things as levers, buttons, linkages, steering wheels, pedals, joysticks, etc. In addition, where user interface system 128 includes a touch sensitive display screen (or another display screen), the operator input mechanisms can include such things as icons, links, etc., which can be actuated with a touch gesture, with a point and click device, or in other ways. Further, when the operator interface system 128 includes speech recognition components, then the operator input mechanisms can include a microphone and corresponding speech recognition logic that can be used to recognize commands or other speech inputs provided by operator 108.

In addition, when operator 108 controls mobile machine 106, remotely, through a remote control station, then the remote control station illustratively interacts with the operator interface system 124 in order to perform the control operations. In another example, the remote control station can communicate with the control system 130 or with other items.

Sensors 132 can be any of a wide variety of different types of sensors. For instance, they can include position sensors (such as a global positioning system—GPS—receiver), a ground speed sensor, an orientation or other pose sensor, various types of engine and actuator sensors, and a wide variety of different types of machine sensors, performance sensors, environment sensors, and other sensors.

Control system 130 illustratively receives operator inputs from operator 108, and sensors 132 and can also receive inputs from image processing system 104. In turn, it generates control signals and applies those control signals to controllable subsystems 134 to control those controllable subsystems based upon the operator or other inputs, and/or the inputs from sensors 132. The controllable subsystems 134 can include a propulsion subsystem 138 which, itself, can include an engine or other power source that is used to drive ground-engaging elements (e.g., tracks, wheels, etc.) on mobile machine 106, through a transmission or directly, to drive movement of mobile machine 106. The controllable subsystems 134 can also include a steering subsystem 140 that includes steering actuators that are used to steer mobile machine 106. They can include automation subsystems 142 that can be activated in order to perform different types of automation on mobile machine 106. Those automation subsystems can include such things as cruise control, automated steering control automated grade control, and a wide variety of other things.

Pattern recognition system 110, in image processing system 104, illustratively receives an image from image capture device 102. It identifies one or more different patterns in that image so the patterns can be correlated to operator identities to identify the operator 108 based upon the recognized pattern. For instance, where the image is a facial image of operator 108, then pattern recognition system 110 illustratively includes facial recognition logic that identifies facial characteristics of operator 108 based upon the facial image. Where the image is a retinal scan image, then pattern recognition system 110 identifies retinal characteristics of operator 108 based on the retinal scan. Pattern recognition system 110 can be any other desired pattern recognition system that recognizes patterns in the captured image, that can be used to identify operator 108, or different characteristics of operator 108 (such as his or her attentiveness, fatigue level, etc.). Some of these are described in greater detail below.

Once the operator 108 is identified, or the characteristics of the operator are identified, that information is provided to authentication system 112 and machine/operator monitoring system 120. For instance, authentication system 112 can analyze the characteristics provided by pattern recognition system 110, and identify operator 108 based on that analysis. Authentication system 112 can also perform a variety of different types of processing based on that information. For instance, it can determine whether this particular operator 108 is authorized to operate mobile machine 106. If not, it can generate a control signal that is provided to mobile machine 106, that indicates this. In turn, control system 130 on mobile machine 106 can lock the operator compartment, the propulsion subsystem 138, the steering subsystem 140, or other subsystem(s) so that mobile machine 106 is not operational.

In doing this, authentication system 112 illustratively accesses operator information 116 corresponding to the identified operator 108. For instance, it may be that operator information 116 has been previously generated and downloaded (or uploaded) to data store 114. That information may indicate the different machines that operator 108 is authorized to operate, the particular functionality on those machines that operator 108 is authorized to operate, the skill level of operator 108, the historical productivity of operator 108, the preferred machine settings for operator 108 (such as the preferred actuator sensitivity level, the preferred seat position, control settings, machine settings, etc.).

Even assuming that authentication system 112 authenticates that operator 108 has permission to operator mobile machine 106, it may be that authentication system 112 also identifies other conditions under which operator 108 can operator machine 106. For instance, if operator 108 is a relatively inexperienced operator, then operator 108 may be authorized to only operate certain functionality on machine 106, or to operate the machine 106 with a certain sensitivity level or at a predefined maximum speed, etc. In that case, system 112 provides an output to mobile machine 106 which is used by control system 130 in order to perform the desired control operations. For instance, control system 130 may only unlock the authorized functionality (which operator 108 is authorized to use), it may set the sensitivity level, or maximum operational speed, accordingly, it may switch on certain automation subsystems 142, or it may perform other desired operations.

Machine/operator monitoring system 120 can also be configured to perform continued monitoring on machine 106, and operator 108, even after operator 108 is authenticated. For instance, it may be that system 120 controls image capture device 102 to intermittently capture additional images of operator 108, during operation. It can then perform processing on those images in order to identify different characteristics of operator 108. Those characteristics may include such things as the position of the gaze of operator 108, the attentiveness of operator 108 (e.g. whether operator 108 is distracted using a mobile device, not looking in an appropriate direction, etc.), the fatigue level of operator 108, or other items, some of which are described in more detail below.

FIG. 2A is a block diagram showing one example of authentication system 112, in more detail. In the example shown in FIG. 2A, authentication system 112 illustratively includes pattern analysis logic 150, operator identification logic 152, data store accessing logic 154, authentication output generator logic 156, and it can include a wide variety of other items 158. Pattern analysis logic 150 illustratively receives the pattern and characteristics recognized by pattern recognition system 110 and can compare it to other patterns or characteristics (which may be stored in data store 114 or elsewhere). Operator identification logic 152 determines whether the pattern matches any other patterns, to identify operator 108. For instance, there may be a plurality of stored patterns or characteristics of patterns that correspond to different operators. By matching the recognized pattern (or characteristics of the recognized pattern) against the stored patterns, the particular operator 108 from which the image was captured can be identified by operator identification logic 152.

Once the identity of operator 108 is known, data store accessing logic 154 illustratively accesses the operator information 116 for that operator. The information can include a wide variety of different types of information, such as permissions or authorized functionality for the operator, operator preferences in terms of various settings, control settings or machine settings that will automatically be generated based upon the identity of operator 108, or other items.

Authentication output generator logic 156 then generates an output indicative of the operator information 116. The output can be, for instance, a control output that is provided to control system 130 in mobile machine 106 in order to control various subsystems 134 based upon the operator information 116 corresponding to operator 108. The output can be the operator information itself, which may be further processed by control system 130 to generate control signals, or it can take other forms.

FIG. 2B is a block diagram showing one example of machine/operator monitoring system 120, in more detail. In the example shown in FIG. 2B, machine/operator monitoring system 120 illustratively includes operator position logic 160, operator fatigue logic 162, operator attentiveness logic 164, gaze tracking logic 166, repetitive operation logic 168, machine operation logic 170, machine position/configuration logic 172, productivity sensing logic 174, and it can include a wide variety of other items 176. Operator position logic 160 illustratively identifies a position of operator 108, relative to the operator compartment of machine 106, based upon a captured image. For instance, it can verify whether the operator is seated in the seat, with the seatbelt latched, whether the operator is exiting the mobile machine, standing outside the mobile machine, etc. This may be used in order to determine which functions of mobile machine 106 to unlock or make inoperable.

Operator fatigue logic 162 illustratively identifies a fatigue level of the operator, based upon the captured images. By way of example, it can count the number of times the operator blinks his or her eyes in a certain period of time. It can determine whether the operator is falling asleep, or about to fall asleep, based upon movement in the operator's head position. It can identify fatigue in other ways as well.

Operator attentiveness logic 164 illustratively identifies where the operator is directing his or her attention. By way of example, it may be that logic 164 is configured to identify when the operator is looking in an appropriate direction, given the specific machine operation being performed. It may identify whether the operator is distracted by looking at a mobile device, or for some other reason.

Gaze tracking logic 166 illustratively tracks the movement of the eyes of operator 108 to determine where operator 108 is looking, and it can also identify gestures of operator 108. This can be useful, for instance, when displaying a diagnostic trouble code (DTC) or other alert message. If tracking logic 166 determines that the operator's eyes have seen the displayed message or that the operator has provided a specific gesture (such as a head nod) after looking at the DTC or alert message, then the message may be dismissed from the display or the display may be otherwise modified. This is just one example.

Repetitive operation logic 168 determines when the operator is performing a repetitive operation. For instance, if mobile machine 106 is an agricultural machine, it may be that the operator is performing a headland turn. This type of operation may involve the operator lifting a ground-engaging implement out of the ground, slowing the vehicle down, turning the vehicle and moving eight rows in one direction or the other, then lowering the ground-engaging implement and increasing machine speed. Repetitive operation logic 168 illustratively identifies when this is occurring so that the operator's control inputs can be recorded, and automatically repeated (or replayed to the control system 130) the next time the operation is to be performed.

Machine operation logic 170 uses the image to identify a particular type of work that the machine is performing. By way of example, it may be that operator 108 is using the machine 106 to perform an unauthorized operation. For instance, it may be that a grader is being used to remove concrete or a sidewalk. This can be determined if the image captured by the device is of an external area near the machine, by way of example. This information can be used to control communication subsystem 141 to send an alert to a manager in other ways.

Machine position/configuration logic 172 illustratively identifies characteristics of the machine position or configuration based upon the captured image. By way of example, an image of an operator or of an operator compartment may be analyzed to determine whether the door to the operator compartment is open or closed. It may identify the position or configuration of other items on the machine as well. This information can be used to control machine 106 as well.

Productivity sensing logic 174 illustratively senses productivity information while machine 106 is being operated by this operator. For instance, when machine 106 is a loader, there may be weight and/or volume sensors 132 on the machine to sense the amount of material that is moved with each load (in terms of weight and/or volume). There may also be sensors 132 to count the number of loads moved. In that case, the productivity of the identified operator can be determined by receiving sensor inputs from sensors 132 and using sensing logic 174 to sense and aggregate the productivity metrics for operator 108. They can then be aggregated with any other information for operator 108, because the machine knows it is operator 108 who is operating the machine.

It will be appreciated that machine/operator monitoring system 120 can include a wide variety of other items 176. Those described herein are described for the sake of example only.

Figure 2C:
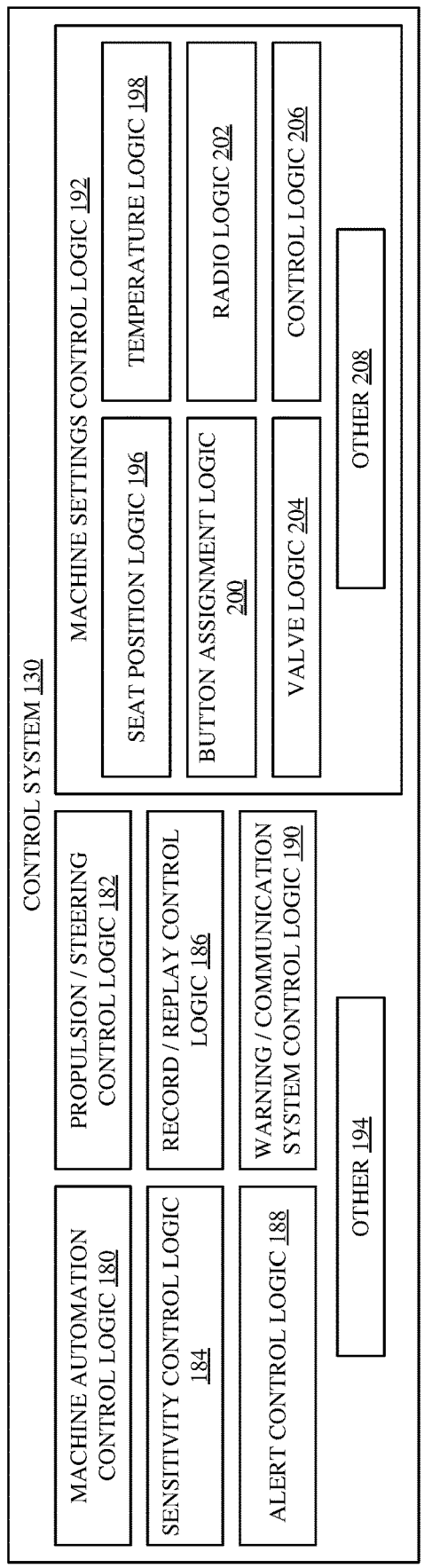
FIG. 2C is a block diagram showing one example of a control system, in more detail.

FIG. 2C is a block diagram showing one example of control system 130 on machine 106. In the example shown in FIG. 2C, control system 130 illustratively includes machine automation control logic 180, propulsion/steering control logic 182, sensitivity control logic 184, record/replay control logic 186, alert control logic 188, warning/communication system control logic 190, machine settings control logic 192, and it can include a wide variety of other items 194. Machine settings control logic 192, itself, can include seat position logic 196, temperature logic 198, button assignment logic 200, radio logic 202, valve logic 204, control logic 206, and it can include other items 208.

Machine automation control logic 190 illustratively receives a signal from image processing system 104 and can control automation subsystems 142. For instance, if the operator is a relatively inexperienced operator, then logic 180 can switch on speed control, steering control, grade control, or other automation systems to assist the operator. Where the operator is relatively experienced, then these automation subsystems may not be automatically switched on, but the decision of which subsystems to use may be left to the operator. This is just one example.

Propulsion/steering control logic 182 illustratively controls the propulsion and steering subsystems 138 and 140, respectively, based upon information from image processing system 104. By way of example, if operator fatigue logic 162 generates an output indicating that the operator is falling asleep, or has fallen asleep, then propulsion/steering control logic 182 may generate a control signal to control the propulsion system to stop movement of machine 106. Where attentiveness logic 164 generates an output indicating that the operator is inattentive (or distracted), then logic 182 may generate a control signal controlling the steering subsystem 140 to automatically steer a desired course, and to control the propulsion subsystem 138 to slow the vehicle down, until the operator is no longer inattentive or distracted.

Sensitivity control logic 184 can generate a control signal to control the sensitivity settings of various actuators on machine 106. By way of example, where the machine is controlled using a joystick input, the sensitivity of the joystick may be set relatively high (or at a relatively highly sensitivity level) if the operator is a relatively experienced operator. However, if the operator is inexperienced, or distracted, or for some other reason, then sensitivity control logic 184 can generate a control signal to automatically reduce the sensitivity of the joystick. These are examples only and the sensitivity of a wide variety of other actuators and operator input mechanisms can be controlled, in a wide variety of different ways.

Machine settings control logic 192 can generate control signals to control, or set, a wide variety of different machine settings, based upon the information generated by image processing system 104. For instance, authentication system 112 may provide an indication of the preferred settings for the identified operator 108, or the permissible settings for that operator. In that case, seat position logic 196 may set the seat position in the operating compartment of machine 106 to a pre-defined position, based upon the operator preference. Temperature logic 198 may control the heating and cooling subsystem in machine 106 in order to set a desired temperature, which is preferred by operator 108 and indicated by the operator information 116.

It may also be that user input buttons in machine 106 are assignable to different functions. In that case, it may be that operator 108 has provided a preferred button assignment assigning the various buttons to various different functions, or that assignment may have been recorded and stored (as operator information 146) by control system 130 last time operator 108 set the assignment. Button assignment logic 200 can thus pre-assign the buttons to those functions, based upon the operator information 116 corresponding to the identified operator 108.

Radio logic 202 may assign the radio buttons to certain stations and tune the radio to a desired station, and valve logic 204 may control electro-hydraulic valve settings or other valve settings based upon the identity of the operator.

Control logic 206 can set a wide variety of different control settings on machine 106 based upon the identity of operator 108, and the operator information 116 corresponding to that operator. On an agricultural harvester, for instance, it may automatically set fan speed settings, sieve and chaffer opening settings, rotor speed settings, machine speed settings and a wide variety of other settings.

Record/replay control logic 186 can receive an indication from machine/operator monitoring system 120 indicating that the machine is about to perform a repetitive operation. In that case, where the repetitive operation is to be recorded, record/replay control logic 186 can record the operator inputs (using operator input sensors on the various operator input mechanisms, or in other ways). The recorded information can be identified and stored in data store 126, or elsewhere.

If the repetitive operation is to be replayed, then logic 186 detects this and can generate control signals to retrieve that information from the data store 126 (or another data store) and generate control signals to control the various controllable subsystems 134 to repeat that stored, repetitive operation.

Alert control logic 188 illustratively controls the various alert and diagnostic trouble code messages that may be displayed or otherwise surfaced for operator 108. By way of example, assuming that a trouble code is displayed indicating that maintenance will be due shortly on the machine. Alert control logic 188 may receive an input from gaze tracking logic 166 indicating that the operator has seen the alert, and performed a gesture (such as nodded his or her head, etc.) indicating that he or she has seen the alert. In that case, the alert can be removed from the display (or other operator interface mechanism) without the operator 108 needing to remove his or her hands from the other controls.

Warning/communication system control logic 190 can generate a warning and communicate it to a manager/or other remote system. For instance, when machine operation logic 170 identifies that the machine is performing an operation that is not authorized, then logic 190 can generate a warning indicating this, and can also control communication subsystem 141 to communicate that warning to a remote system.

These are just examples of how control system 130 can be used. Other items 194 can generate a wide variety of other control signals as well.

Figure 3A:
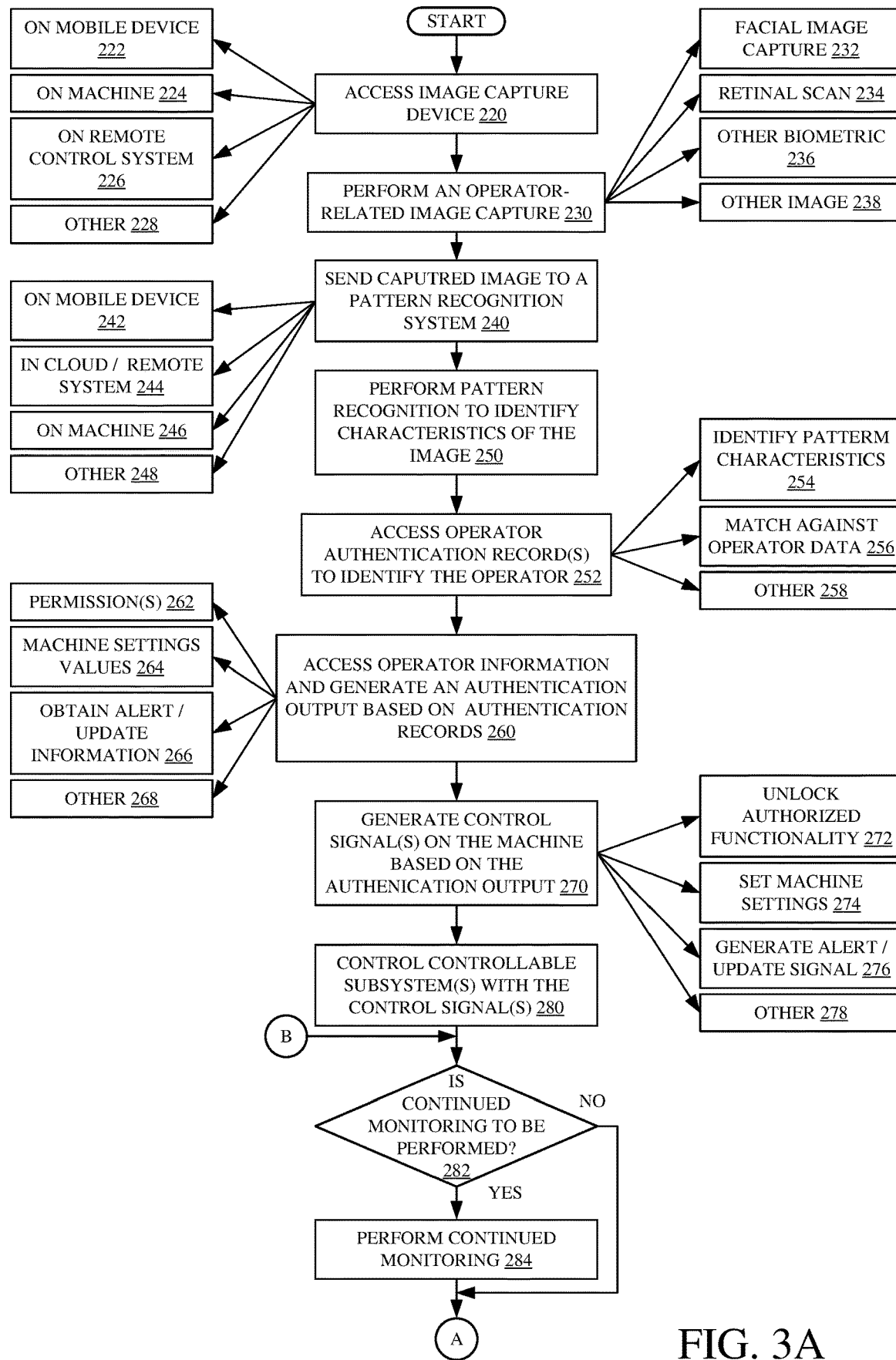

FIGS. 3A and 3B (collectively referred to herein as FIG. 3) show a flow diagram illustrating one example of the operation of the architecture 100 illustrated in FIG. 1 (and the various items illustrated in FIGS. 2A-2C) in capturing one or more images using image capture device 102, processing those images with image processing system 104 and controlling mobile machine 106 based upon the processed images. Image processing system 104 first accesses the image capture device 102, in order to control it to capture an image of operator 108. It can do this automatically, or it can instruct operator 108 to operate image capture device 102 to capture and send an image to image processing system 104. The image capture device 102 can be controlled in other ways, and by other components as well. Accessing image capture device 102 is indicated block 220 in the flow diagram of FIG. 3. It will be noted that the image capture device 102 may be on a mobile device as indicated by block 222, on machine 106 as indicated by block 224, on a remote control station or remote control system, as indicated by block 226, or on another device as indicated by block 228.

Image capture device 102 then performs an operator-related image capture in order to capture an operator-related image. This is indicated by block 230. For instance, it can perform a facial image capture capturing a facial image of operator 108. This is indicated by block 232. It can perform a retinal scan capturing a retinal image as indicated by block 234. It can capture other biometric data in other operator-related images, as indicated by block 236. It can also capture a wide variety of other types of images as well, and this is indicated by block 238.

The image is then received at pattern recognition system 110. The image can be sent by image capture device 102, or retrieved by pattern recognition system 102, or it can be received in other ways. Receiving the captured image at pattern recognition system 110 is indicated by block 240 in the flow diagram of FIG. 3. As discussed above, the pattern recognition system 110 (an indeed the image processing system 104) can be located on a mobile device as indicated by block 242. It can be located in the cloud or in another remote computing system as indicated by block 244. It can be located on mobile machine 106 as indicated by block 246, or in other locations (such as a remote control station or other location) as indicated by block 248.

Pattern recognition system 110 then performs pattern recognition to identify characteristics of the image. This is indicated by block 250 in the flow diagram of FIG. 3. For instance, where the image is a facial image, it can identify patterns or other characteristics in that image. If it is a retinal scan, it can identify characteristics of that image as well.

The recognized characteristics are then provided to authentication system 112 which accesses operator authentication records (which may be in data store 114 or elsewhere) in order to identify the operator. This is indicated by block 252. Pattern analysis logic 150 can identify the pattern characteristics and operator identification logic 152 can match those characteristics against operator data to identify the particular operator. This is indicated by blocks 254 and 256 in the flow diagram of FIG. 3. The operator 108 can be identified in other ways, based upon the pattern information recognized in the image, and this is indicated by block 258.

Data store accessing logic 154 (in authentication system 112) then accesses operator information 116 in data store 114 and authentication output generator logic 156 generates an authentication output based upon that information. This is indicated by block 260 in the flow diagram of FIG. 3. The output can be indicative of operator information 116, or it can be control outputs derived from that information. For instance, the output can identify permissions that are granted to this operator 108, which may indicate the particular functionality on machine 106 that should be unlocked. Generating an output indicative of operator permissions is indicated by block 262. The output may identify the machine settings, or include control signals that are used to set those machine settings. This is indicated by block 264. The authentication system may obtain and output alert or update information for this operator, as indicated by block 266. For instance, the update information may be indicative of the operator's performance to date, on this particular machine. It may indicate a comparison of how the operator is performing (in terms of productivity) relative to other operators. It may output an indication of how the operator is operating in terms of safety, speed, efficiency, or a wide variety of other metrics.

The authentication output based upon the operator information 116 (or authentication records or other data in that information) can be generated in a wide variety of other ways as well. This is indicated by block 268.

Control system 130 then generates control signals to control machine 106, based upon the output from authentication system 112. This is indicated by block 270 in the flow diagram of FIG. 3. For instance, any of the logic described above with respect to FIG. 2C can generate control signals to control machine 106 in the corresponding ways. Some examples include controlling mobile machine 106 to unlock authorized functionality, or authorized subsystems 134. This is indicated by block 272. Machine settings control logic 192 can generate control signals to set machine settings as indicated by block 274. Alert control logic 188 can generate control signals to generate alerts and updates as indicated by block 276. The control system 130 can generate a wide variety of other control signals to control mobile machine 106 based upon the output from authentication system 112. This is indicated by block 278 in the flow diagram of FIG. 3.

Control system 130 then applies those control signals to the controllable subsystems 134 in order to control the controllable subsystems 134 using those control signals. This is indicated by block 280.

It may also be that machine/operator monitoring system 120 is provided and configured to perform continued monitoring of operator 108, during machine operation. If this is the case, as indicated by block 282, then continued monitoring is performed by system 120. This is indicated by block 284 and one example of this is described in greater detail below with respect to FIG. 4. The operation continues, in this way, until the operation is complete. This is indicated by block 286 in the flow diagram of FIG. 3.

Figure 4:
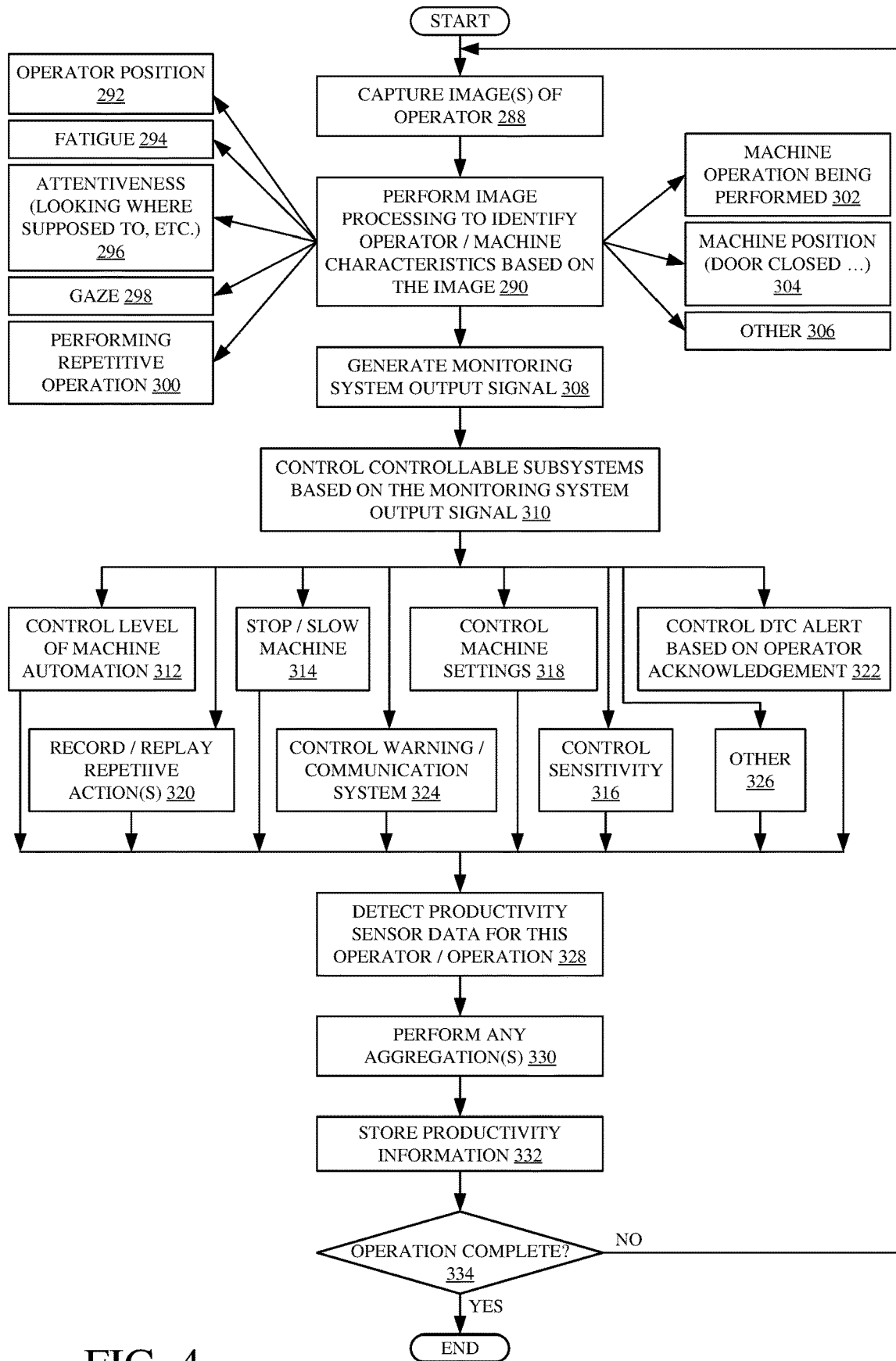
FIG. 4 is a flow diagram showing one example of the operation of a machine/operator monitoring system, and control system.

FIG. 4 is a flow diagram illustrating one example of the operation of machine/operator monitoring system 120 in generating information that is used to control mobile machine 106, based upon the continued operation of machine 106 by operator 108. Image capture device 102 captures additional images of operator 108 in order to perform this type of monitoring. This is indicated by block 288. The images can be captured intermittently or periodically, or on some other time-based criteria. In another example, they can be captured based on other criteria, such as a change in the operator's physical position, a change in the performance or control inputs to machine 106, or in other ways.

Once the additional images are captured, pattern recognition system 110 again performs image processing to identify operator/machine characteristics based upon the images. This is indicated by block 290. For instance, system 110 can generate outputs which are used by operator position logic 160 to identify the position of operator 108 (such as whether the operator is sitting in the seat, etc.). This is indicated by block 292.

The outputs from pattern recognition system 110 may allow operator fatigue logic 162 to determine a fatigue level of the operator. For instance, if the operator's head is bent over, or if the operator is frequently blinking or has his or her eyes closed for extended periods of time, or has stopped moving (indicating that the operator may be sleeping) these may provide an indication as to the fatigue level of the operator. Identifying operator fatigue based on the image is indicated by block 294.

The output of system 110 may allow operator attentiveness logic 164 to generate an output indicative operator attentiveness. This may be generated based upon an analysis of where the operator is looking (relative to where he or she is supposed to be looking), or in other ways. Generating an output indicative of operator attentiveness is indicated by block 296.

The outputs from system 110 may allow gaze tracking logic 166 to track the gaze of operator 108. This may be indicative of where the operator is looking, whether he or she has seen certain alerts, diagnostic trouble codes, etc. Identifying the operator gaze is indicated by block 298. The outputs may allow repetitive operation logic 168 to determine that operator 108 is about to perform, or is performing, a repetitive operation. This was discussed above, and detecting these characteristics is indicated by block 300. The outputs may provide information that allows machine operation logic 170 to identify the particular machine operation that is being performed. For instance, an image may be taken of the vicinity around machine 106 to identify the type of surface the machine is operating on, among other things. Identifying characteristics indicative of the type of machine operation is indicated by block 302. The information may allow machine position/configuration logic 172 to identify the position of the machine (such as whether a door is open, or other things). This is indicated by block 304. The information can be used by other monitor logic to identify operator or machine characteristics in a wide variety of other ways as well, and this is indicated by block 306.

Machine/operator monitoring system 120 then generates an output signal indicative of the monitoring information identified by the various items of logic in machine/operator monitoring system 120. Generating the output signal is indicated by block 308 in the flow diagram of FIG. 4.

The monitoring system output signal can be provided to mobile machine 106, in a variety of different ways. For instance, it can be provided as an input to control system 130. Regardless of how it is received by machine 106, control system 130 illustratively uses it to generate control systems that can be used to control one or more of the controllable subsystems 134 based upon the monitor system output signal. This is indicated by block 310 in the flow diagram of FIG. 4.

By way of example, machine automation control logic 180 can control automation subsystems 142 to control the different levels of automation that are activated on machine 106. Some examples of this were discussed above, and it is indicated by block 312 in the flow diagram of FIG. 4.

Propulsion/steering control logic 182 can control the propulsion and steering subsystems to slow or stop the machine, or to control the steering of the machine, or to control them in other ways. This is indicated by block 314.

Sensitivity control logic 184 can generate a control signal to set the sensitivity of the various subsystems. As discussed above, this can be done based upon the experience level of the operator, based upon currently identified operator characteristics (such as fatigue, distractedness, etc.). Controlling the sensitivity is indicated by block 316 in the flow diagram of FIG. 4.

Machine settings control logic 192 can generate control signals to control various settings on machine 106. For instance, it can automatically control seat position, radio station, valve settings, cab temperature, button assignment, or other control settings. Controlling the machine settings is indicated by block 318.

Record/replay control logic 186 can generate control signals to record or replay a repetitive operation. For instance, it can record the operator inputs when the operator is about to perform a repetitive operation, and it can automatically play those inputs back in order to automatically control machine 106 to perform the repetitive operation, when it is time. Generating control signals to record and replay repetitive actions is indicated by block 320.

Alert control logic 188 can generate control signals to control diagnostic trouble code alerts based on operator acknowledgement or other characteristics. For instance, when system 120 sends an output indicating the operator has seen and dismissed an alert message (such as using a head gesture) then alert control logic 188 can control the user interface display in order to dismiss that alert. This is indicated by block 322.

Warning/communication system control logic 190 can also generate control signals to generate a warning (e.g., that the machine 106 is being used improperly) and send that warning to a remote system (such as a manager's system or elsewhere). Controlling the warning and communication subsystem 141 is indicated by block 324 in the flow diagram of FIG. 4. Control signals can be generated based on an output from machine/operator monitoring system 120 in a wide variety of other ways, to control a wide variety of other controllable subsystems. This is indicated by block 326.

Also, in one example, productivity sensing logic 174 detects productivity sensor data for this particular operator/operation. For instance, once the operator 108 is identified by authentication system 112, then productivity metrics can be sensed and aggregated in a variety of different ways, for this operator. They can be sensed at a relatively fine granularity (such as an amount of material moved per digging operation) or they can be aggregated and generated on a less granular level (such as the amount of material moved, per gallon of fuel used, for this operator, for this shift). Detecting productivity sensor data for this operator and/or operation is indicated by block 328. Performing any aggregations or other processing on that information is indicated by block 330. At some point, machine/operator monitoring system 120 can store the productivity information either on data store 114 or data store 126, or a remote data store. This is indicated by block 332.

This type of monitoring can be performed by machine/operator monitoring system 120 until the current operation is complete, or until the system is turned off, or until other criteria are met. Continuing the operation in this way is indicated by block 334 in the flow diagram of FIG. 4.

The present discussion has mentioned processors and servers. In one embodiment, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

FIG. 5 is a block diagram of architecture 100, shown in FIG. 1, except that it communicates with elements in a remote server architecture 500. In an example, remote server architecture 500 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown in FIG. 1 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 5, some items are similar to those shown in FIG. 1 and they are similarly numbered. FIG. 5 specifically shows that image capture device 102 and image processing subsystem 104 can reside in a variety of different location, such as on a mobile device 504, at a remote work station 506, on machine 106, in cloud 502, or elsewhere. Therefore, harvester 100 accesses those systems through remote server location 502.

FIG. 5 also depicts another example of a remote server architecture. FIG. 5 shows that it is also contemplated that some elements of FIG. 1 are disposed at remote server location 502 while others are not. By way of example, data store 114 or pattern recognition system 110 can be disposed at a location separate from location 502, and accessed through the remote server at location 502. Regardless of where they are located, they can be accessed directly by items 106, 504 and/or 506, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another mobile machine (such as a fuel truck) can have an automated information collection system. As the machine 106 comes close to the fuel truck for fueling, the system automatically collects the information from the machine 106 using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the machine 106 until the machine 106 enters a covered location. The machine 106, itself, can then send the information to the main network.

It will also be noted that the elements of FIG. 1, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 6:
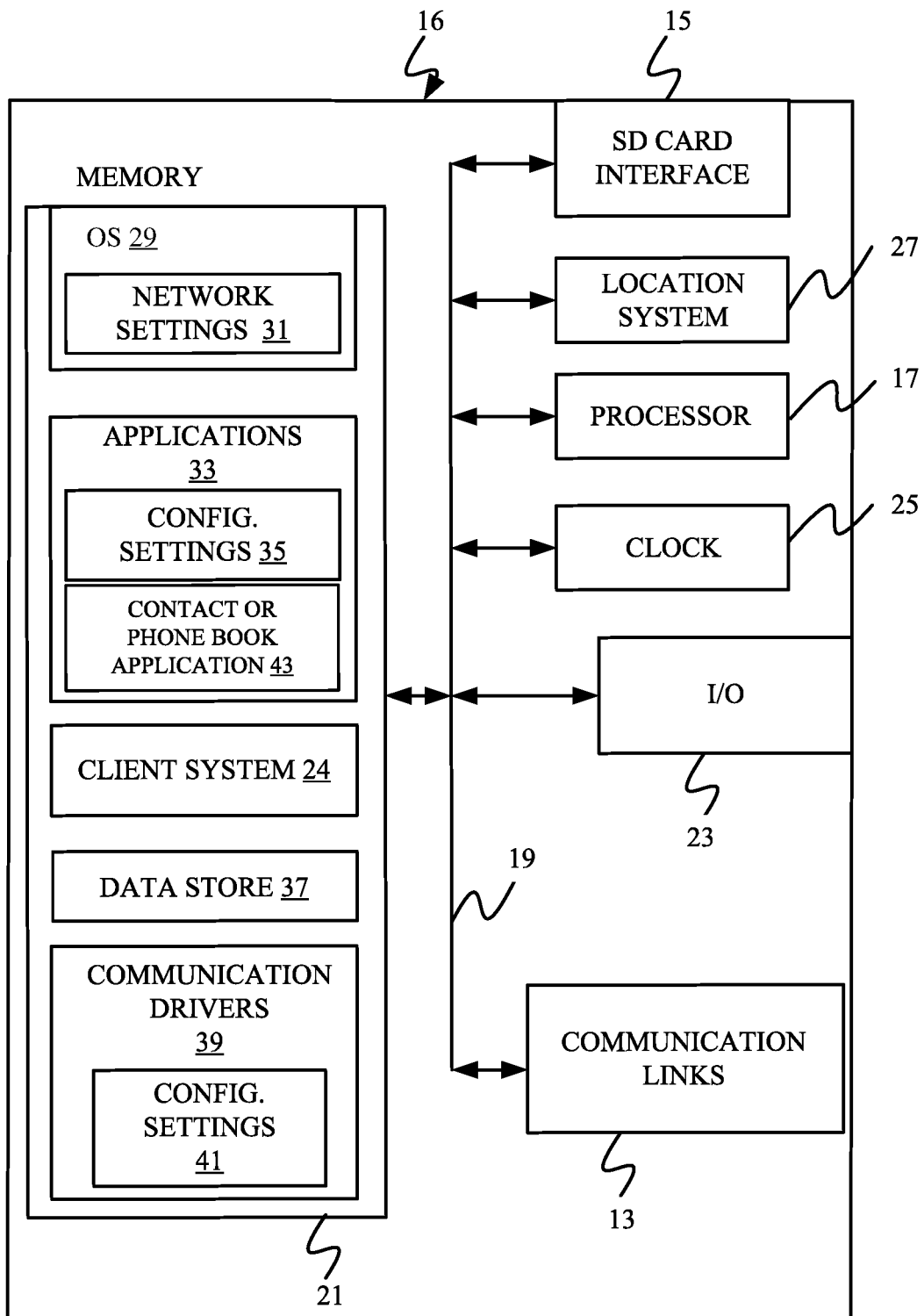
FIGS. 6-8 show examples of mobile devices that can be used in the architectures shown in the previous figures.
Figure 7:
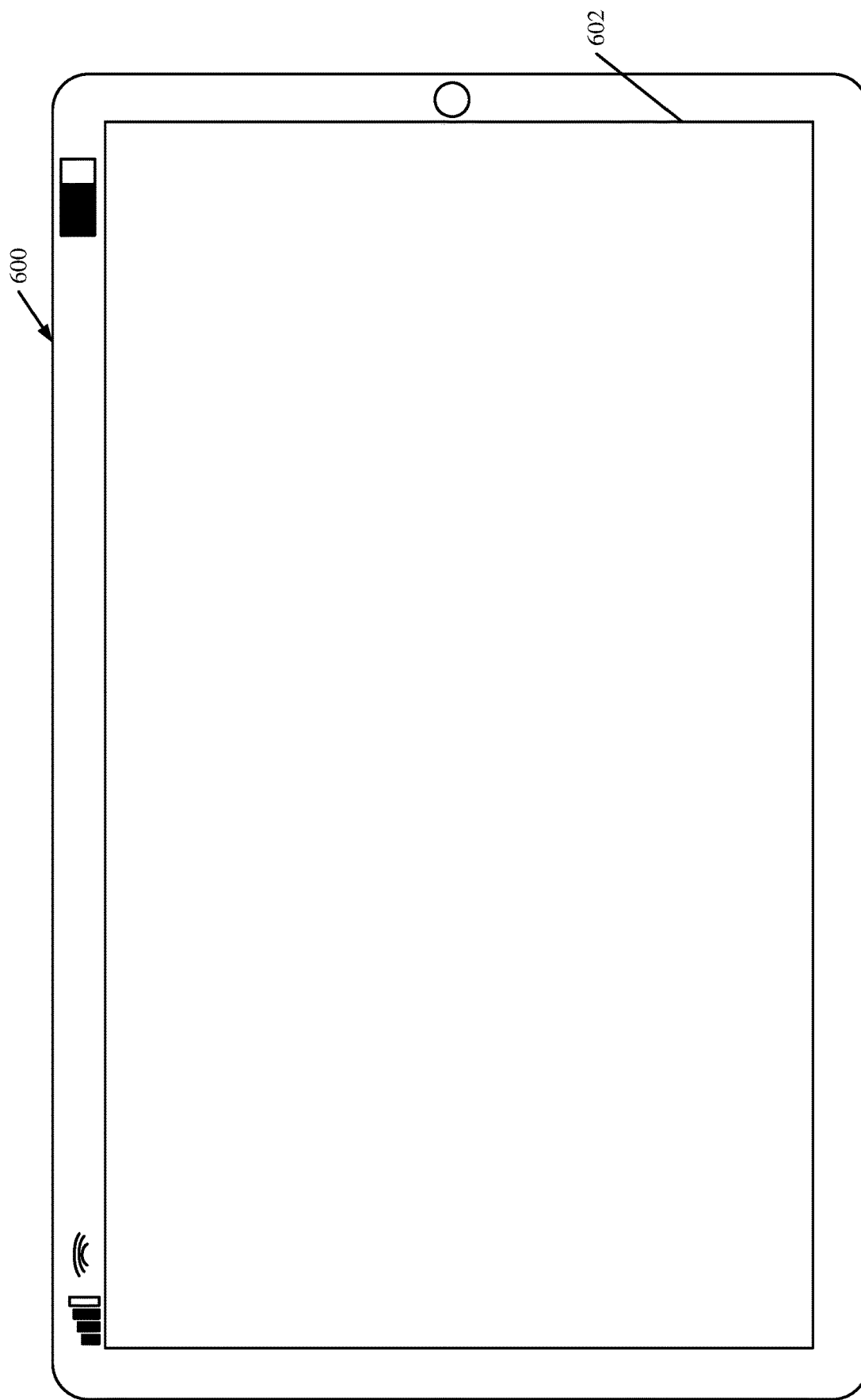
Figure 8:
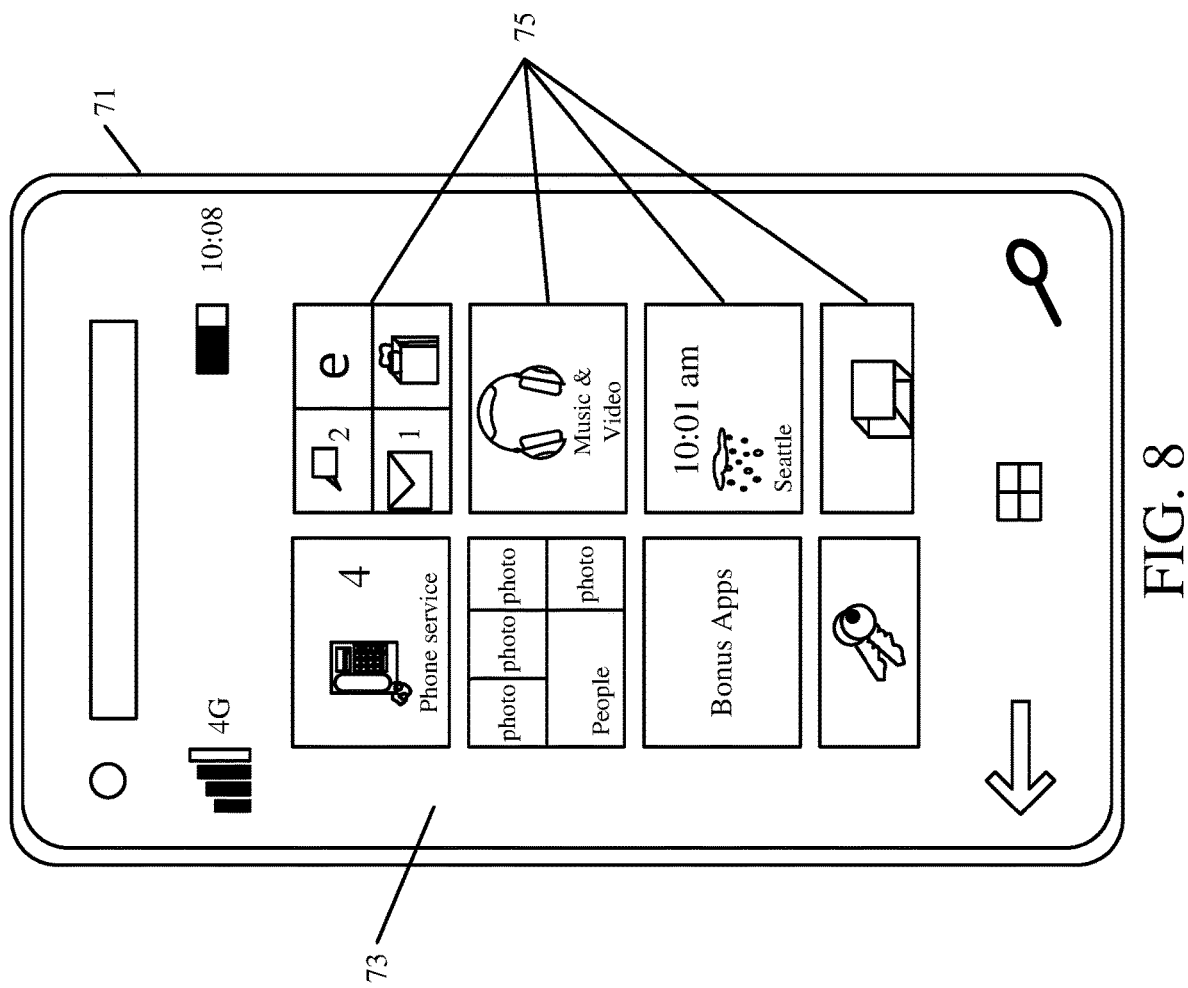

FIG. 6 is a simplified block diagram of one illustrative example of a handheld or mobile computing device that can be used as a user's or client's hand held device 16, in which the present system (or parts of it) can be deployed. For instance, a mobile device can be deployed in the operator compartment of machine 106 for use in receiving inputs, generating, processing, or displaying the information. FIGS. 7-8 are examples of handheld or mobile devices.

FIG. 6 provides a general block diagram of the components of a client device 16 that can run some components shown in FIG. 1, that interacts with them, or both. In the device 16, a communications link 13 is provided that allows the handheld device to communicate with other computing devices and in some examples provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody processors from previous FIGS.) along a bus 19 that is also connected to memory 21 and input/output (I/O) components 23, as well as clock 25 and location system 27.

I/O components 23, in one example, are provided to facilitate input and output operations. I/O components 23 for various examples of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. It can also include computer storage media (described below). Memory 21 stores computer readable instructions that, when executed by processor 17, cause the processor to perform computer-implemented steps or functions according to the instructions. Processor 17 can be activated by other components to facilitate their functionality as well.

FIG. 7 shows one example in which device 16 is a tablet computer 600. In FIG. 7, computer 600 is shown with user interface display screen 602. Screen 602 can be a touch screen or a pen-enabled interface that receives inputs from a pen or stylus. It can also use an on-screen virtual keyboard. Of course, it might also be attached to a keyboard or other user input device through a suitable attachment mechanism, such as a wireless link or USB port, for instance. Computer 600 can also illustratively receive voice inputs as well.

FIG. 8 shows that the device can be a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 9:
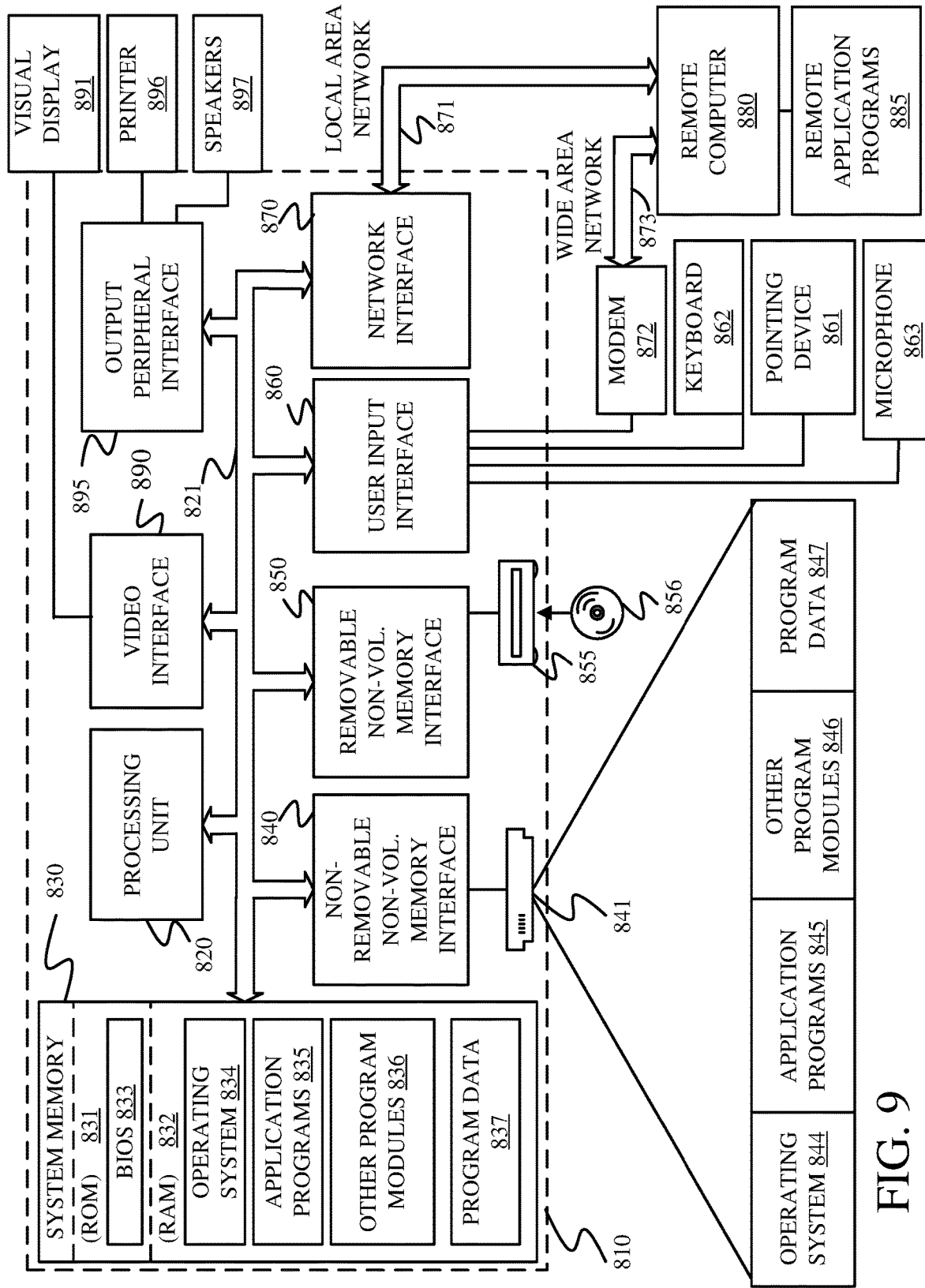
FIG. 9 is a block diagram showing one example of a computing environment that can be used in the architectures shown in the previous figures.

FIG. 9 is one example of a computing environment in which elements of FIG. 1, or parts of it, (for example) can be deployed. With reference to FIG. 9, an example system for implementing some embodiments includes a computing device in the form of a computer 810. Components of computer 810 may include, but are not limited to, a processing unit 820 (which can comprise a processor or server from previous FIGS.), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 1 can be deployed in corresponding portions of FIG. 9.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 9 illustrates operating system 834, application programs 835, other program modules 836, and program data 837.

The computer 810 may also include other removable/non-removable volatile/nonvolatile computer storage media. By way of example only, FIG. 9 illustrates a hard disk drive 841 that reads from or writes to non-removable, nonvolatile magnetic media, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 9, provide storage of computer readable instructions, data structures, program modules and other data for the computer 810. In FIG. 9, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 9 illustrates, for example, that remote application programs 885 can reside on remote computer 880.

It should also be noted that the different embodiments described herein can be combined in different ways. That is, parts of one or more embodiments can be combined with parts of one or more other embodiments. All of this is contemplated herein.

Example 1 is a mobile work machine, comprising:
a controllable subsystem;
a pattern recognition system that receives image data indicative of an image of an operator, captured by an image capture device;
an authentication system that identifies a characteristic of the operator based on the image data;
authentication output generator logic that generates an authentication system output indicative of control data, based on the identified characteristic of the operator; and
a control system that generates a control signal to control the controllable subsystem based on the control data.

Example 2 is the mobile work machine of any or all previous examples wherein the controllable subsystem includes lockable machine functionality and wherein the authentication system comprises:
data store accessing logic configured to access a data store to obtain a set of permissions, corresponding to the operator, based on the identified characteristic of the operator.

Example 3 is the mobile work machine of any or all previous examples wherein the control system is configured to generate the control signal to unlock machine functionality on the controllable subsystem based on the set of permissions.

Example 4 is the mobile work machine of any or all previous examples wherein the controllable subsystem includes an automation subsystem that is activated to perform an automated control operation and wherein the control system is configured to generate the control signal to control activation of the automation subsystem based on the characteristic of the operator.

Example 5 is the mobile work machine of any or all previous examples wherein the controllable subsystem includes controllable machine settings and wherein the control system comprises:
machine settings control logic configured to generate a control signal to set the controllable machine settings based on the characteristic of the operator.

Example 6 is the mobile work machine of any or all previous examples wherein the controllable subsystem includes a set of assignable buttons that are assignable to different functions, wherein the machine settings control logic comprises:
button assignment logic configured to generate a control signal to automatically control function assignment to the assignable buttons based on the characteristic of the operator.

Example 7 is the mobile work machine of any or all previous examples wherein the controllable subsystem includes an operator input mechanism with a sensitivity setting wherein the control system comprises:
sensitivity control logic configured to generate a sensitivity setting control signal to automatically set the sensitivity setting of the operator input mechanism to a sensitivity based on the characteristic of the operator.

Example 8 is the mobile work machine of any or all previous examples wherein the pattern recognition system is configured to receive image data from a plurality of images of the operator, captured by an image capture device during operation of the mobile work machine, and further comprising:
a machine/operator monitoring system configured to monitor a performance related quality of the operator based on the image data from the plurality of images.

Example 9 is the mobile work machine of any or all previous examples wherein the machine/operator monitoring system comprises:
operator attentiveness logic configured to generate an operator attentiveness value indicative of operator attentiveness wherein the control system generates the control signal to control the controllable subsystem based on the operator attentiveness value.

Example 10 is the mobile work machine of any or all previous examples wherein the machine/operator monitoring system comprises:
operator fatigue logic configured to generate an operator fatigue value indicative of operator fatigue wherein the control system generates the control signal to control the controllable subsystem based on the operator fatigue value.

Example 11 is the mobile work machine of any or all previous examples wherein the machine/operator monitoring system comprises:
operator gesture logic configured to generate an operator gesture signal indicative of an operator gesture wherein the control system generates the control signal to control the controllable subsystem based on the operator gesture signal.

Example 12 is a computer implemented method of controlling a mobile work machine, comprising:
receiving image data indicative of an image of an operator, captured by an image capture device;
identifying a characteristic of the operator based on the image data;
generating an authentication system output indicative of control data, based on the identified characteristic of the operator; and generating a control signal to control a controllable subsystem on the mobile work machine based on the control data.

Example 13 is the computer implemented method of any or all previous examples wherein the controllable subsystem includes lockable machine functionality and wherein generating the authentication system output comprises:

accessing a data store to obtain a set of permissions, corresponding to the operator, based on the identified characteristic of the operator.

Example 14 is the computer implemented method of any or all previous examples wherein generating the control signal comprises:

generating the control signal to unlock machine functionality on the controllable subsystem based on the set of permissions.

Example 15 is the computer implemented method of any or all previous examples wherein the controllable subsystem includes an automation subsystem that is activated to perform an automated control operation and wherein generating the control signal comprises generating the control signal to control activation of the automation subsystem based on the characteristic of the operator.

Example 16 is the computer implemented method of any or all previous examples wherein the controllable subsystem includes controllable machine settings and wherein generating the control signal comprises:

generating a control signal to set the controllable machine settings based on the characteristic of the operator.

Example 17 is the computer implemented method of any or all previous examples wherein receiving image data comprises receiving image data from a plurality of images of the operator, captured by an image capture device during operation of the mobile work machine, and further comprising:

monitoring a performance related quality of the operator based on the image data from the plurality of images and wherein generating the control signal comprises generating the control signal based on the performance related quality.

Example 18 is a mobile work machine control system, comprising:

a pattern recognition system that receives image data indicative of an image of an operator of a mobile work machine, captured by an image capture device;

an authentication system that identifies a characteristic of the operator based on the image data;

authentication output generator logic that generates an authentication system output indicative of control data, based on the identified characteristic of the operator; and a control system that generates a control signal to control a controllable subsystem on the mobile work machine based on the control data.

Example 19 is the mobile work machine control system of any or all previous examples wherein the pattern recognition system is configured to receive image data from a plurality of images of the operator, captured by an image capture device during operation of the mobile work machine, and further comprising:

a machine/operator monitoring system configured to monitor a performance related quality of the operator based on the image data from the plurality of images, wherein the control system is configured to generate the control signal to control a controllable subsystem based on the performance related quality.

Example 20 is the mobile work machine control system of any or all previous examples wherein the machine/operator monitoring system comprises:

repetitive operation logic that detects when the operator is performing a repetitive operation, the control system including record/replay control logic configured to record operator inputs during the repetitive operation and replay the recorded operator inputs when the operator performs a subsequent iteration of the repetitive operation.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A mobile work machine, comprising:
    a plurality of controllable subsystems, at least one of the plurality of controllable subsystems including an operator input mechanism with a sensitivity setting;
    a pattern recognition system that receives image data indicative of an image of an operator, captured by an image capture device;
    an authentication system that identifies a characteristic of the operator based on the image data;
    authentication output generator logic that generates an authentication system output indicative of control data, based on the identified characteristic of the operator; and
    a control system that generates a sensitivity setting control signal to automatically set the sensitivity setting of the operator input mechanism based on the control data.

2. The mobile work machine of claim 1 wherein at least one of the plurality of controllable subsystems includes lockable machine functionality and wherein the authentication system comprises:
    data store accessing logic configured to access a data store to obtain a set of permissions, corresponding to the operator, based on the identified characteristic of the operator.

3. The mobile work machine of claim 2 wherein the control system is configured to generate a control signal to unlock the lockable machine functionality based on the set of permissions.

4. The mobile work machine of claim 1 wherein at least one of the plurality of controllable subsystems includes an automation subsystem that is activated to perform an automated control operation and wherein the control system is configured to generate a control signal to control activation of the automation subsystem based on the characteristic of the operator.

5. The mobile work machine of claim 1 wherein at least one of the plurality of controllable subsystems includes controllable machine settings and wherein the control system comprises:
    machine settings control logic configured to generate a control signal to set the controllable machine settings based on the characteristic of the operator.

6. The mobile work machine of claim 5 wherein at least one of the plurality of controllable subsystems includes a set of assignable buttons that are assignable to different functions, wherein the machine settings control logic comprises:
    button assignment logic configured to generate a control signal to automatically control function assignment to the assignable buttons based on the characteristic of the operator.

7. The mobile work machine of claim 1 wherein the pattern recognition system is configured to receive image data from a plurality of images of the operator, captured by an image capture device during operation of the mobile work machine, and further comprising:
  a machine/operator monitoring system configured to monitor a performance related quality of the operator based on the image data from the plurality of images.

8. The mobile work machine of claim 7 wherein the machine/operator monitoring system comprises:
  operator attentiveness logic configured to generate an operator attentiveness value indicative of operator attentiveness wherein the control system generates a control signal to control at least one of the plurality of controllable subsystems based on the operator attentiveness value.

9. The mobile work machine of claim 7 wherein the machine/operator monitoring system comprises:
  operator fatigue logic configured to generate an operator fatigue value indicative of operator fatigue wherein the control system generates a control signal to control at least one of the plurality of controllable subsystems based on the operator fatigue value.

10. The mobile work machine of claim 7 wherein the machine/operator monitoring system comprises:
  operator gesture logic configured to generate an operator gesture signal indicative of an operator gesture wherein the control system generates a control signal to control at least one of the plurality of controllable subsystems based on the operator gesture signal.

11. A computer implemented method of controlling a mobile work machine, comprising:
  receiving image data from a plurality of images of an operator, captured by an image capture device;
  identifying a characteristic of the operator based on image data from at least one of the plurality of images;
  identifying an identity of the operator based on the characteristic of the operator;
  generating an authentication system output indicative of control data, based on the identity of the operator;
  generating an operator gesture signal indicative of an operator gesture based on one or more of the plurality of images; and
  generating a control signal to control at least one of a plurality of controllable subsystems on the mobile work machine based on the control data and the operator gesture signal.

12. The computer implemented method of claim 11 wherein at least one of the plurality of controllable subsystems includes lockable and unlockable machine functionality and wherein generating the authentication system output comprises:
  accessing a data store to obtain a set of permissions, corresponding to the operator, based on the identity of the operator.

13. The computer implemented method of claim 12 and further comprising:
  generating an authorization control signal to unlock the lockable machine functionality.

14. The computer implemented method of claim 11 wherein at least one of the plurality of controllable subsystems includes an automation subsystem that is activated to perform an automated control operation and further comprising:
  identifying an experience level of the operator, based on the identity of the operator;
  and generating an automation subsystem activation control signal control signal to control activation of the automation subsystem based on the experience level of the operator.

15. The computer implemented method of claim 11 wherein at least one of the plurality of controllable subsystems includes controllable machine settings and further comprising:
  generating a machine settings control signal to set the controllable machine settings based on the identity of the operator.

16. The computer implemented method of claim 13 wherein receiving image data includes receiving image data from at least one of the plurality of images of the operator, captured by the image capture device during operation of the mobile work machine, and further comprising:
  monitoring a performance related quality of the operator based on the image data from the at least one image of the plurality of images; and
  generating the authorization control signal comprises generating the authorization control signal based on the performance related quality.

17. A mobile work machine control system, comprising:
  a pattern recognition system that receives image data indicative of an image of an operator of a mobile work machine, captured by an image capture device;
an authentication system that:
  identifies the operator as a particular operator, of a plurality of different operators, based on the image data;
  identifies authorized functionality of the mobile work machine for the particular operator, based on the identification of the operator as the particular operator; and
  generates an authentication system output indicative of control data, based on the identified authorized functionality; and
  a control system that generates an automation subsystem activation control signal to control activation of a plurality of automation subsystems associated with a plurality of controllable subsystems on the mobile work machine based on the control data.

18. The mobile work machine control system of claim 17 wherein the pattern recognition system is configured to receive image data from a plurality of images of the operator, captured by an image capture device during operation of the mobile work machine, and further comprising:
  a machine/operator monitoring system configured to monitor a performance related quality of the operator based on the image data from the plurality of images, wherein the control system is configured to generate a control signal to control at least one of the plurality of controllable subsystems based on the performance related quality.

19. The mobile work machine control system of claim 18 wherein the machine/operator monitoring system comprises:
  repetitive operation logic that detects when the operator is performing a repetitive operation, the control system including record/replay control logic configured to record operator inputs during the repetitive operation and repeat the recorded operator inputs to control the mobile work machine during a subsequent iteration of the repetitive operation.

* * * * *